US010280131B2

(12) United States Patent
Foley et al.

(10) Patent No.: US 10,280,131 B2
(45) Date of Patent: May 7, 2019

(54) TERPENE-DERIVED ACIDS AND ESTERS AND METHODS FOR PREPARING AND USING SAME

(71) Applicant: P2 SCIENCE, INC., Woodbridge, CT (US)

(72) Inventors: Patrick Foley, New Haven, CT (US); Yonghua Yang, New Haven, CT (US); Robert Bedoukian, Danbury, CT (US); Thomas Killinger, Danbury, CT (US)

(73) Assignee: P2 SCIENCE, INC., Woodbridge, CT (US)

( * ) Notice: Subject to any disclaimer, the term of this patent is extended or adjusted under 35 U.S.C. 154(b) by 0 days.

(21) Appl. No.: 15/620,493

(22) Filed: Jun. 12, 2017

(65) Prior Publication Data

US 2017/0275230 A1 Sep. 28, 2017

Related U.S. Application Data

(62) Division of application No. 15/111,143, filed as application No. PCT/US2015/011272 on Jan. 13, 2015, now Pat. No. 9,682,914.

(60) Provisional application No. 61/926,813, filed on Jan. 13, 2014.

(51) Int. Cl.
*C07C 67/08* (2006.01)
*C07C 51/34* (2006.01)
*C07C 45/40* (2006.01)
*C07C 51/285* (2006.01)
*C07C 45/85* (2006.01)
*A23L 27/20* (2016.01)
*C07C 59/125* (2006.01)
*C07C 69/708* (2006.01)
*C11B 9/00* (2006.01)

(52) U.S. Cl.
CPC ............ *C07C 67/08* (2013.01); *A23L 27/202* (2016.08); *C07C 45/40* (2013.01); *C07C 45/85* (2013.01); *C07C 51/285* (2013.01); *C07C 51/34* (2013.01); *C07C 59/125* (2013.01); *C07C 69/708* (2013.01); *C11B 9/0019* (2013.01); *A23V 2002/00* (2013.01)

(58) Field of Classification Search
CPC ....... C07C 67/08; C07C 59/125; C07C 45/85; C07C 47/198; C07C 45/40; C07C 51/285; C07C 51/34; C07C 69/708; C07C 69/533; A23L 27/202; A23V 2002/00; C11B 9/0019

See application file for complete search history.

(56) References Cited

U.S. PATENT DOCUMENTS

| 2,813,113 A | 11/1957 | Goebel et al. |
| 3,023,244 A | 2/1962 | Eschinasi |
| 3,699,169 A | 10/1972 | Bertele et al. |
| 4,296,258 A | 10/1981 | Fehr et al. |
| 4,311,617 A | 1/1982 | Ansari et al. |
| 4,491,537 A | 1/1985 | Futoshi et al. |
| 4,791,228 A | 12/1988 | Siclari et al. |
| 4,940,808 A | 7/1990 | Schulz et al. |
| 5,543,565 A | 8/1996 | McVay et al. |
| 5,756,821 A | 5/1998 | Dilk et al. |
| 5,801,275 A | 9/1998 | McVay et al. |
| 6,309,521 B1 | 10/2001 | Andrews et al. |
| 6,395,695 B1 | 5/2002 | Sivik |
| 6,512,131 B1 | 1/2003 | Best et al. |
| 6,545,186 B2 | 4/2003 | Giselbrecht et al. |
| 6,548,715 B1 | 4/2003 | Bouillion et al. |
| 7,825,277 B2 | 11/2010 | Gutsche et al. |
| 7,968,742 B2 | 6/2011 | Aigner et al. |
| 8,221,708 B2 | 7/2012 | Seebauer et al. |
| 9,035,091 B2 | 5/2015 | Foley et al. |
| 9,604,898 B2 | 3/2017 | Foley et al. |
| 9,682,914 B2 | 6/2017 | Foley et al. |
| 10,011,582 B2 | 7/2018 | Foley et al. |
| 10,071,944 B2 | 9/2018 | Foley et al. |
| 2003/0078453 A1 | 4/2003 | Springer et al. |
| 2003/0100781 A1 | 5/2003 | Springer et al. |
| 2004/0186042 A1 | 9/2004 | Schmaus et al. |
| 2007/0010688 A1 | 1/2007 | Ko et al. |
| 2007/0142666 A1 | 6/2007 | Himeno et al. |
| 2007/0276165 A1 | 11/2007 | Gutsche et al. |
| 2009/0221083 A1* | 9/2009 | White .................. C07F 15/025 436/127 |
| 2013/0078685 A1 | 3/2013 | Ulrich et al. |
| 2013/0177497 A1 | 7/2013 | Fitch et al. |
| 2013/0338150 A1 | 12/2013 | Boehme et al. |
| 2014/0316149 A1 | 10/2014 | Wickens et al. |
| 2015/0183707 A1 | 7/2015 | Foley et al. |
| 2017/0247314 A1 | 8/2017 | Foley et al. |

FOREIGN PATENT DOCUMENTS

| CA | 1144561 | 4/1983 |
| CN | 102653531 A | 9/2012 |
| CN | 102795987 A | 11/2012 |

(Continued)

OTHER PUBLICATIONS

STN Mar. 7, 2013 1 page (Year: 2013).*
STN Sep. 29, 2005 1 page (Year: 2005).*
Ayer et al. (Degraded monoterpenes from the opisthobranch mollusc Melibe leonina1, Short Communications, Experientia 39, Birkhauser Verlag, CH-4010 Basel/Switzerland, published 1983) 1-2 pages (Year: 1983).*
William published 2001 1-4 pages (Year: 2001).*
Cahn, R. S. et al. "Specification of Molecular Chirality" *Angew. Chem. Inter. Edit.* 1966, vol. 5, No. 4, p. 385-415.

(Continued)

*Primary Examiner* — Yevgeny Valenrod
*Assistant Examiner* — Blaine G Doletski
(74) *Attorney, Agent, or Firm* — Hoxie & Associates LLC

(57) ABSTRACT

The invention relates to terpene-derived acids and esters thereof as well as to processes for synthesizing them.

5 Claims, 3 Drawing Sheets

(56) References Cited

FOREIGN PATENT DOCUMENTS

| EP | 0761629 A1 | 3/1997 |
|---|---|---|
| JP | H06-135878 | 5/1994 |
| WO | WO 1995/001960 | 1/1995 |
| WO | WO 2002/048431 | 6/2002 |
| WO | WO 2007/068498 | 6/2007 |
| WO | WO 2009/061806 A2 | 5/2009 |
| WO | WO2012/177357 * | 12/2012 |
| WO | WO 2013/053102 A1 | 4/2013 |
| WO | WO 2015/039010 | 3/2015 |
| WO | WO 2015/106293 A1 | 7/2015 |
| WO | WO 2015/126936 | 8/2015 |
| WO | WO 2015/191706 A1 | 12/2015 |
| WO | WO 2015/196019 | 12/2015 |
| WO | WO 2016/091895 | 6/2016 |
| WO | WO 2017/223220 | 12/2017 |
| WO | WO 2018/053289 | 3/2018 |

OTHER PUBLICATIONS

Cahn, R. S. and Ingold, C. K. "Specification of Configuration About Quadricovalent Asymmetric Atoms" *J. Chem. Soc.* 1951 (London), p. 612-622.
Cahn, R. S. et al. "The Specification of Asymmetric Configuration in Organic Chemistry" *Experientia* 1956, vol. 12, p. 81-94.
Cahn, R. S. "An Introduction to the Sequence Rule. A System for the Specification of Absolute Configuration" *Journal of Chemical Education* 1964 (London), vol. 41, No. 3, p. 116-125.
Competition Science Vision Aug. 2000, *Pratiyogita Darpan*, vol. 3, No. 30, p. 799.
Gross, R. A., Jr. "Ozonolysis Problems That Promote Student Reasoning" *Journal of Chemical Education*, vol. 83, No. 4, 2006, p. 604-609.
PubChem-CID-107500001, Oct. 26, 2006, 17 pages.
Willand-Charnley, R. et al. "Pyridine is an Organocatalyst for the Reductive Ozonolysis of Alkenes" *Org Lett.* vol. 14, No. 9, May 2012, p. 2242-2245.
English Abstract of Japanese Publication No. H06-135878, published May 17, 1994.
Abe, et al, "Synthesis of Massoia lactone and its analogs. I. Synthesis of the lactone of 1-decen-4-ol-1-carboxylic acid," 75 Nippon Kagaka Kaishi, Pure Chem., 953-5, (1921-1947), (1954). [CAS Abstract Only].
Avdeev, et al., "Molecular Mechanism of Oxygen Isotopic Exchange over Supported Vanadium Oxide Catalyst Vox/TiO2," The Journal of Physical Chemistry C, vol. 117, No. 6, pp. 2879-2887, (2013).
Cermak, et al., "Synthesis of d-Stearolactone from Oleic Acid," JAOCS, vol. 77, No. 3, pp. 243-248, (2000).
Chen, et al., "A Predictably Selective Aliphatic C—H Oxidation Reaction for Complex Molecule Synthesis," Science, vol. 318, (2007).
Chmielewski, et al., "Organic Syntheses Under High Pressure. 3. General Approach to the Synthesis of Naturally Occuring .delta.-lactones," The Journal of Organic Chemistry, vol. 46, No. 11, pp. 2230-2233, (1981).
Cook, et al., "Study of the Total Synthesis of (−)-Exiguolide," J. Org. Chem.,vol. 77, pp. 6728-6742, (2012).
Dupe, et al., "Methyl Ricinoleate as Platform Chemical for Simultaneous Production of Fine Chemicals and Polymer Precursors," ChemSusChem., vol. 5, pp. 2249-2254, (2012).
Förtsch, et al., "Synthese, Kristallstruktur und Reaktionen neuartiger metallacyclischer Dioxo- und Aminooxocarben-Komplexe des Eisens," Chem. Ber., vol. 127, pp. 711-715, (1994). [English Abstract Only.].
Gerth, et al., "Synthesis of d-Lactones via Radical C—C Bond Formation Using Chiral Radical Precursors," J. Org. Chem., vol. 51, pp. 3726-3729, (1986).
Harding, et al., "beta-Methyl-delta-dodecadiene and beta-Methyl-delta-decadiene," Journal of the Chemical Society, Transactions, pp. 448-451, (1911).
Hearn, et al., "Kinetics and Product Studies for Ozonolysis Reactions of Organic Particles Using Aerosol CIMS," The Journal of Physical Chemistry A, vol. 108, No. 45, pp. 10019-10029, (2004).
Kadesch, R.G., "Ozonolysis of Fatty Acids and Their Derivatives," Progress in the Chemistry of Fats and Other Lipids, vol. 6, pp. 291-312, (1963).
Kauffmann, et al., "Ubergangsmetallaktivierte organische Verbindungen, XXXVIII. Chemoselektive nucleophile Methylierungen durch In-Situ-Blockierung von Aldehydgruppen unter [alpha]1-Phosphonioalkoxid-Bildung," Chemishe Berichte, pp. 459-464, (1993). [No English Translation.].
Kula, et al., "Synthesis of Enantiomerically Pure Volatile Compounds Derived From (R)-3-Hydroxynonanal," Tetrahedron: Asymmetry, vol. 11, pp. 943-950, (2000).
Lee, et al., "Tin-free, Radical-mediated Gamma-alkylations of Alpha, Beta-unsaturated Esters via O-tert-alkyl Dienol Ethers," vol. 1, pp. 49-54, (2008).
Maggiolo, A. "Ozonization of Fatty Acids and Their Derivatives," The Journal of the American Oil Chemists' Society, vol. 40, pp. 161-164, (1963).
Otsubo, et al., "A Direct Synthesis of [gamma]-, [delta], and [epsilon]- Lactones Utilizing SmI2-induced Barbier-type Reaction in the Presence of Hexamethylphosphoric Triamide (HMPA)," Chemistry Letters, pp. 1487-1490, (1987). Http://www.journal.csj.jp/doi/pdf/10.1246/cl.1987.1487 [retrieved on May 29, 2017].
Quan, et al., "A Convenient Protecting Group for Aldehydes," Synlett, vol. 2001, No. 12, pp. 1925-1926, (2001).
Rani, et al., "Ozonolysis of Oleic Acid Over a Nano Vanadium Pentoxide (V2O5) Catalyst," European Journal of Scientific Research, vol. 24, No. 3, pp. 428-432, (2008).
Richardson, et al., "A Practical Synthesis of Long-Chain Iso-Fatty Acids (iso-C12-C19) and Related Natural Products," Beilstein Journal of Organic Chemistry, vol. 9, pp. 1807-1812, (2013).
Rosenberger, et al., "28. Synthesis of d-Lactones From Glutaraldehyde," Helvetica Chimica Acta, vol. 55, pp. 249-255, (1972).
Sabitha, et al., "The First Asymmetric Total Synthesis of (R)-Tuberolactone, (S)-Jasmine Lactone, and (R)-d-Decalactone," Tetrahedron Letters, vol. 47, pp. 8179-8181, (2006).
Schiaffo, C.E., "I. An Improved Procedure for Alkene Ozonolysis. II. Expoloring a New Structural Paradigm for Peroxide Antimalarials," Student Research Projects, Dissertations, and Theses—Chemistry, Department, University of Nebraska-Lincoln, (Jun. 2011), Paper 23.
Shao, et al., "Asymmetric Hydrogenation of 3,5-Dioxoesters Catalyzed by Ru-binap Complex: A Short Step Asymmetric Synthesis of 6-Substituted 5,6-dihyrdo-2-pyrones," Tetrahedron, vol. 49, No. 10, pp. 1997-2010, (1993).
Shekhter, et al., "Study of Compounds with Juvenile-hormone Activity. X. Synthesis of Esters of 2E,4E-3,11-dimethyl-11-methoxy-2,4-dodecadienic and 2E,4E-2, 11-dimethyl-2,4,10-dodecatrienic acids," Zhurnal Organicheskoi Khimii, vol. 15, No. 2, pp. 260-264, (1979). [No English Translation.].
Shono, et al., "Electroreductive Intermolecular Coupling of Ketones with Olefins," J. Org. Chem., vol. 54, No. 26, pp. 6001-6003, (1989).
STN 1984 (Year: 1984), p. 1.
STN Nov. 1984 (Year: 1984), 1 Page.
STN 1995 (Year: 1995), 1 Page.
Surburg, et al., Common Fragrance and Flavor Materials, 5th Ed. Wiley-VCH, pp. 149-172, (2006).
Tanaka, et al., "Syntheses of (5E)-PGE2 and New 6-Functionalized Derivatives by the Use of Palladium-Catalyzed Decarboxylative Allylic Alkylation," Tetrahedron, vol. 42, No. 24, pp. 6747-6758, (1986).
Utaka, et al., "New Synthesis of Jasmine Lactone and Related-d-Lactones from 1,2 Cyclohexanedione. Preparation and Dye-Sensitized Photooxygenation of 3-(2-Alkenyl)- and 3-(2-Alkynyl)-1,2-cyclohexanediones," J. Org. Chem., vol. 51, No. 6, pp. 935-938, (1986).
Wasmi, et al, "Synthesis of Vanadium Pentoxide Nanoparticles as Catalysts for the Ozonation of Palm Oil," Ozone: Science & Engineering, vol. 38, No. 1, pp. 36-41, (2015).

(56) References Cited

OTHER PUBLICATIONS

Yahata, et al., "Methodology for in Situ Protection of Aldehydes and Ketones Using Trimethylsilyl Trifluoromethanesulfonate and Phosphines: Selective Alkylation and Reduction of Ketones, Esters, Amides, and Nitriles," Chem. Pharm. Bull., vol. 61, No. 12, pp. 1298-1307, (2013).

* cited by examiner

TERPENE-DERIVED ACIDS AND ESTERS AND METHODS FOR PREPARING AND USING SAME

CROSS-REFERENCE TO RELATED APPLICATIONS

This application is a divisional application of U.S. patent application Ser. No. 15/111,143, filed Jul. 12, 2016, which is a U.S. National Stage Application under 35 C.F.R. 371 of International Application No. PCT/US2015/011272, filed Jan. 13, 2015, which claims the benefit of and priority to U.S. Provisional Patent Application No. 61/926,813, filed Jan. 13, 2014, titled "TERPENE-DERIVED ACIDS AND ESTERS AND METHODS FOR PREPARING AND USING SAME," the entirety of each of which is incorporated by reference herein for all purposes.

BACKGROUND OF THE INVENTION

Ozonolysis of terpenes and analogs thereof can produce aldehydes that are used as ingredients in flavors and fragrances. See, e.g., U.S. Pat. Nos. 3,023,244, 3,699,169 and 6,545,186, and WO 2013/053102.

It is not uncommon that about 5-30% of the desired aldehydic product from the ozonolysis procedure is over-oxidized to generate the corresponding acid. The over-oxidized acid product is generally regarded as waste. This invention relates to cost-efficient isolation of the acid product and application thereof in industries including, but not limited to, flavorings, fragrances, and preservatives.

SUMMARY OF THE INVENTION

In one aspect, the invention relates to a method of producing a compound of formula (I) or a salt thereof:

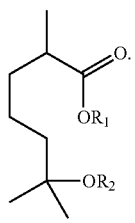

(I)

In this formula, $R_1$ is H, unsubstituted or substituted $C_1$-$C_{10}$ alkyl, or unsubstituted or substituted $C_2$-$C_{10}$ alkenyl, and $R_2$ is H, unsubstituted or substituted $C_1$-$C_{10}$ alkyl, or $COR_a$, in which $R_a$ is H or unsubstituted or substituted $C_1$-$C_{10}$ alkyl.

The method includes reacting a compound having the formula (IB)

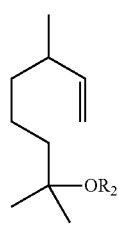

(IB)

with ozone and subsequently with an oxidant different from ozone to obtain the compound of formula (I) wherein $R_1$ is H.

Alternatively, the method includes (1) reacting a compound having the formula (IB)

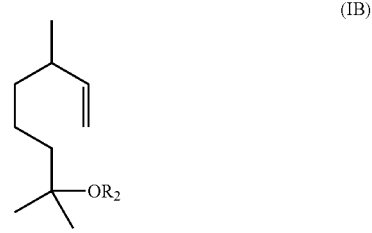

(IB)

with ozone and subsequently with a reductant to obtain a mixture comprising the compound of formula (I) wherein $R_1$ is H and a compound of formula (IC):

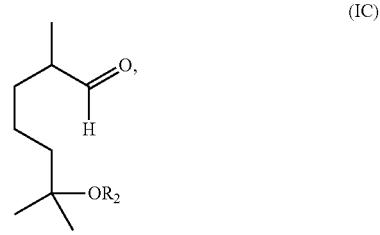

(IC)

and (2) separating the compound of formula (I) wherein $R_1$ is H from the compound of formula (IC).

In another aspect, the invention relates to a method of producing a compound of formula I or a salt thereof, the method including providing an aqueous mixture comprising the compound of formula (I) wherein $R_1$ is H and a compound of formula (IC):

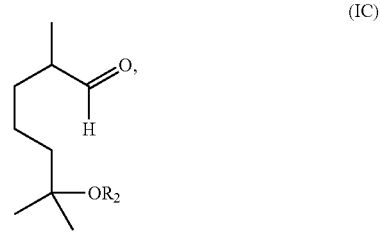

(IC)

adjusting the pH of the aqueous mixture to a first pH value that is between about 6 and about 10 to obtain a first organic phase that comprises the compound of formula (IC) and a first aqueous phase that comprises a salt of compound of formula (I);

separating the first aqueous phase from the first organic phase;

optionally adding an oxidant to the separated first aqueous phase;

adjusting the pH of the first aqueous solution to a second pH value that is not greater than 5 to obtain a second organic phase that comprises the compound of formula (I) wherein $R_1$ is H and a second aqueous phase; and separating the second organic phase from the second aqueous phase to obtain the compound of formula (I) wherein $R_1$ is H.

In one embodiment, the aqueous mixture comprising the compound of formula (I) and the compound of formula (IC) is obtained by ozonolysis of a compound having the formula IB

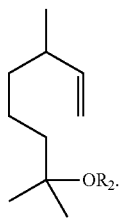
(IB)

The invention also relates to a compound of formula (I), (II), (III), or (IV) below or a salt thereof:

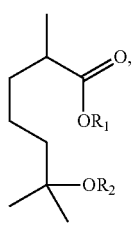
(I)

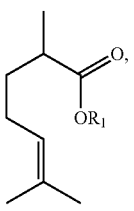
(II)

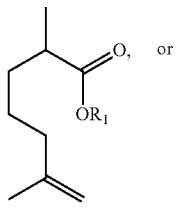
(III)

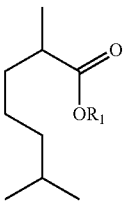
(IV)

wherein $R_1$ is H, unsubstituted or substituted $C_1$-$C_{10}$ alkyl, or unsubstituted or substituted $C_2$-$C_{10}$ alkenyl, and $R_2$ is H, unsubstituted or substituted $C_1$-$C_{10}$ alkyl, or $COR_a$, in which $R_a$ is H or unsubstituted or substituted $C_1$-$C_{10}$ alkyl.

In one embodiment, the salt of a compound of any of formulae described herein, is formed by reacting a —COOH group of the compound with a base to form alkali metal salts such as $Na^+$, $K^+$, $Li^+$, alkali earth metal salts such as $Mg^{2+}$ or $Ca^{2+}$, organic amine salts, or organic phosphonium salts.

The invention also relates to a compound of formula (I), a compound of formula (II), a compound of formula (III), a compound of formula (IV), or a salt thereof, generated by the methods described herein.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. In addition, the materials, methods, and examples are illustrative only and are not intended to be limiting.

Other features and advantages of the invention will be apparent from the figures, the following detailed description, examples, and claims.

DETAILED DESCRIPTION OF THE INVENTION

Figure 1:
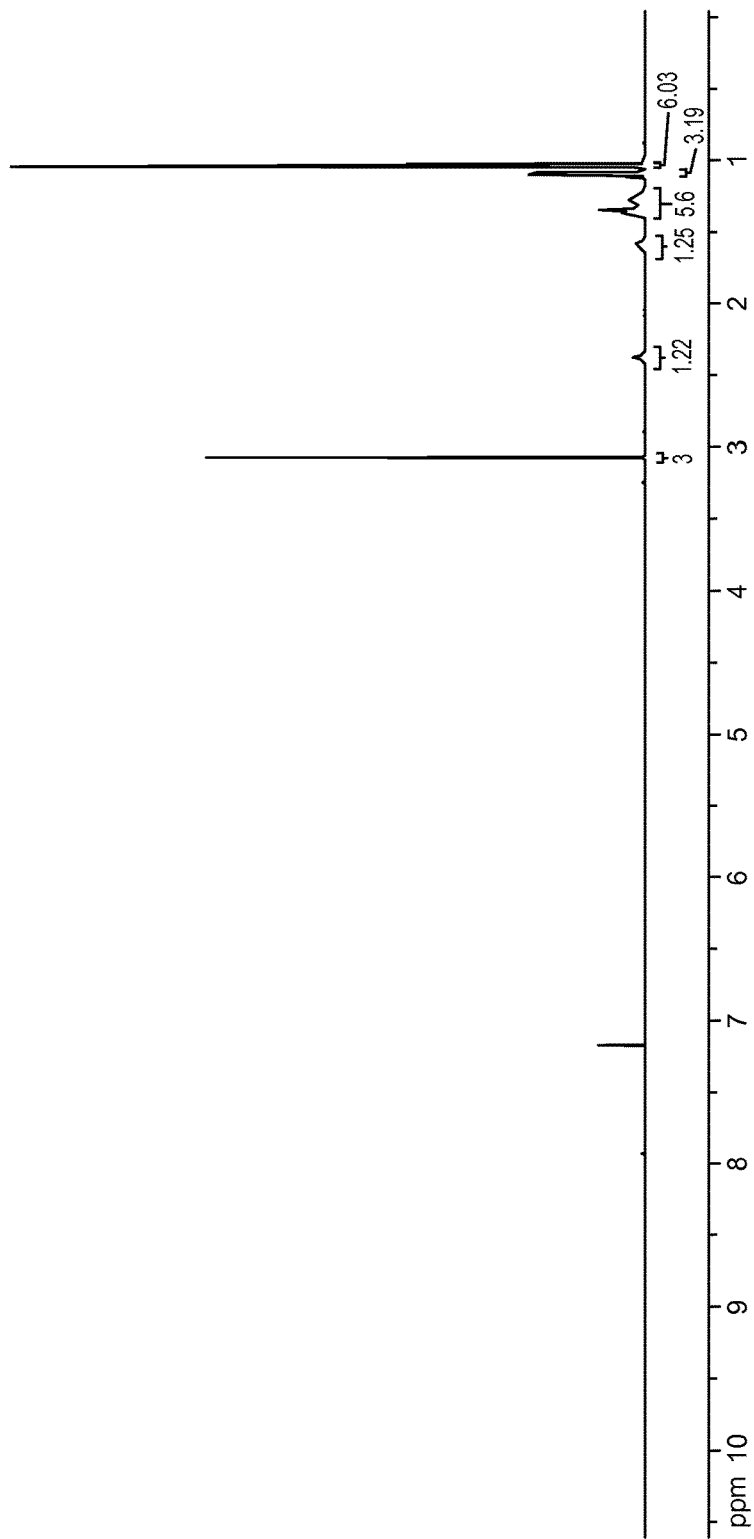
FIG. 1 is a $^1$H NMR spectrum of 6-methoxy-2,6-dimethylheptanoic acid.

Over-oxidation is observed in almost all ozonolysis procedures for generating aldehydes. The over-oxidized product, e.g., the corresponding acid, is generally regarded as waste and therefore negatively impacts the economics of aldehyde production. This invention relates to a cost-efficient isolation process of the acid product and use of the acid to offset or even reverse the negative impact mentioned above.

The invention relates to methods of producing acids and esters from terpenes or terpene analogs. In particular, this invention relates to ozonolysis of hydroxy- and alkoxy-citronellenes, for example 2,6-dimethyloct-7-en-2-ol and 7-methoxy-3,7-dimethyloct-1-ene, and producing an acid from either a reductive or oxidative ozonolysis procedure. This invention further relates to the derivatization of the acid to produce an ester, an unsaturated or saturated acid, or ester thereof. The compounds produced by the methods described herein can be used in flavors and fragrances due to their unique aroma properties.

Methods of Synthesis

In one aspect, the invention relates to a method of synthesizing a compound of formula (I) or a salt thereof:

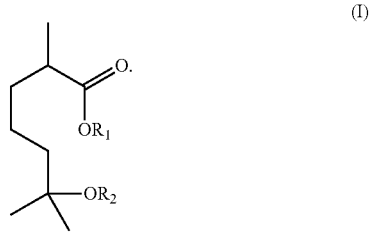
(I)

In this formula, $R_1$ is one of H, an unsubstituted or substituted $C_1$-$C_{10}$ alkyl, or an unsubstituted or substituted $C_2$-$C_{10}$ alkenyl, and $R_2$ is one of H, an unsubstituted or substituted $C_1$-$C_{10}$ alkyl, or $COR_a$, in which $R_a$ is one of H or an unsubstituted or substituted $C_1$-$C_{10}$ alkyl.

The method includes reacting a compound having the formula (IB)

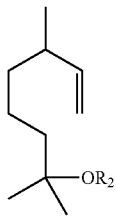
(IB)

with ozone and subsequently with an oxidant (i.e., an oxidizing agent) different from ozone, to obtain the compound of formula (I) wherein $R_1$ is H.

Alternatively, the method may include reacting a compound having the formula (IB) with ozone and subsequently with a reductant (i.e., a reducing agent) to obtain a mixture comprising the compound of formula (I) wherein $R_1$ is H and a compound of formula (IC):

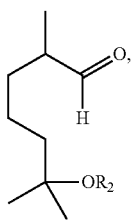
(IC)

and separating the compound of formula (I) wherein $R_1$ is H from the compound of formula (IC).

In another aspect, the invention relates to a method of producing a compound of formula (I) or a salt thereof, the method including providing an aqueous mixture comprising the compound of formula (I) wherein $R_1$ is H and a compound of formula (IC):

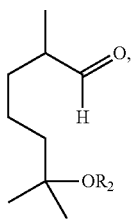
(IC)

adjusting the pH of the aqueous mixture to a first pH value that is between about 6 and about 10 to obtain a first organic phase that comprises the compound of formula (IC) and a first aqueous phase that comprises a salt of compound of formula (I);

separating the first aqueous phase from the first organic phase;

optionally adding an oxidant to the separated first aqueous phase;

adjusting the pH of the first aqueous solution to a second pH value that is not greater than about 5 to obtain a second organic phase that comprises the compound of formula (I) wherein $R_1$ is H and a second aqueous phase; and separating the second organic phase from the second aqueous phase to obtain the compound of formula (I) wherein $R_1$ is H.

In some embodiments, the aqueous mixture comprising the compound of formula (I) and the compound of formula (IC) may be obtained by ozonolysis of a compound having the formula (IB)

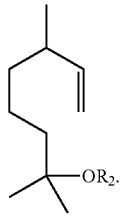
(IB)

In some embodiments, the reaction of the compound of formula (IB) with ozone or the ozonolysis of the compound of formula (IB) may be carried out in the presence of a solvent. The solvent may comprise water, an organic solvent or a mixture there of. For example, the solvent may comprise water and one or more organic solvents. The organic solvent may be an acid, an alcohol, or a mixture thereof. For example, the organic solvent may be acetic acid, nonanoic acid, propanoic acid, palmitic acid, myristic acid, lauric acid, octanoic acid, methanol, isopropanol, ethanol, or mixtures thereof.

In some embodiments, the reaction of the compound of formula (IB) with ozone may be carried out in the absence of a solvent such as water and an organic solvent.

In some embodiment, the mixture comprising the compound of formula (I) wherein $R_1$ is H and the compound of formula (IC) is an aqueous mixture.

In one embodiment, separating the compound of formula (I) from the compound of formula (IC) may be performed by:

adjusting the pH of the aqueous mixture to a first pH value that is between about 6 and about 10 to obtain a first organic phase that comprises the compound of formula (IC) and a first aqueous phase that comprises a salt of compound of formula (I);

separating the first aqueous phase from the first organic phase;

optionally adding an oxidant to the separated first aqueous phase;

adjusting the pH of the first aqueous solution to a second pH value that is not greater than about 5 (e.g., not greater than 4, or pH=0-4) to obtain a second organic phase that comprises the compound of formula (I) wherein $R_1$ is H and a second aqueous phase; and separating the second organic phase from the second aqueous phase to obtain the compound of formula (I) wherein $R_1$ is H.

In some embodiments, an oxidant, such as a peroxide or any other suitable oxidant, may be added to the first aqueous phase before the pH is adjusted to not greater than 5 (e.g., not greater than 4, or pH=0-4).

In some embodiments, the method may further include reacting the compound of formula (I) wherein $R_1$ is H, with an alcohol having the formula $R_bOH$, wherein $R_b$ is an unsubstituted or substituted $C_1$-$C_{10}$ alkyl or an unsubstituted or substituted $C_2$-$C_{10}$ alkenyl, to produce a compound of formula (I) wherein $R_1$ is an unsubstituted or substituted $C_1$-$C_{10}$ alkyl, or an unsubstituted or substituted $C_2$-$C_{10}$ alkenyl.

In some embodiments, the method may further include performing an elimination reaction on the compound of formula (I) to obtain a compound of formula II or III or a mixture thereof:

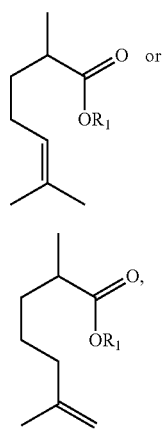

(II)

(III)

wherein $R_1$ is one of H, an unsubstituted or substituted $C_1$-$C_{10}$ alkyl, or an unsubstituted or substituted $C_2$-$C_{10}$ alkenyl. For example, the elimination reaction may be performed in a solvent comprising an alcohol, including but not limited to methanol, ethanol, isopropanol, butanol and the like), and an acid, including but not limited to p-toluenesulfonic acid or tosic acid, at a suitable temperature, which may be, for example, room temperature.

In some embodiments in which an oxidant is used, the oxidant may be a peroxide, and may, for example, be hydrogen peroxide.

In some embodiments in which a reductant is used, the reductant may be a reducing agent suitable for producing an aldehyde in a reductive ozonolysis process. For example, the reductant may be $H_2$, and may be in the presence or absence of a suitable catalyst. If present, the catalyst may include, but is not limited to, Pd, Ni, Rh, Pt, and Ru. For example, the reductant may be sodium bisulfite ($NaHSO_3$). For example, the reductant may be triphenylphosphine, thiourea, zinc dust, or dimethyl sulfide. An example of the methods of the invention are illustrated in Schemes 1 and 2 below. $R_1$ and $R_2$ in Schemes 1 and 2 are as defined herein for formula (I) unless otherwise specified.

Scheme 1

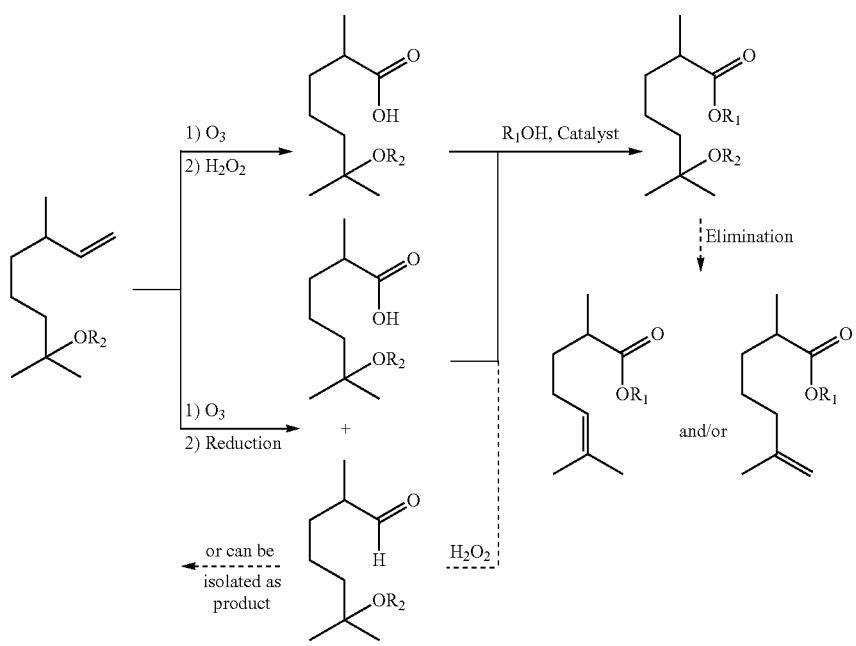

----- = an optional step to products

In Scheme 1 above, the terpene-derived acid or ester product can be formed via either oxidative (top route) or reductive (bottom route) ozonolysis of methoxycitronellene, hydroxycitronellene, acetoxycitronellene, or alkoxycitronellenes. When the acid and the corresponding aldehyde are formed in the reductive ozonolysis procedure (bottom route), the acid can be separated from the aldehydic product by bringing the pH to between about 6 and about 10, for example, from between about 7 and about 10, to form the salts of the terpene-derived acids, as shown, for example, in Scheme 2 below.

phase comprising the aldehyde, and an aqueous phase comprising the salt of the acid, as illustrated in Scheme 2 above. Following phase separation, hydrogen peroxide or any other suitable oxidant can be added to the aqueous phase to convert any trace aldehyde present in the aqueous phase into the corresponding acid and/or acid salt. Once the acid salt product has been isolated in the aqueous phase, the pH value of the aqueous phase can be adjusted such that the target acid is formed and phase separated from the aqueous phase. Additional organic extraction can be performed if needed to obtain an additional amount of the target acid.

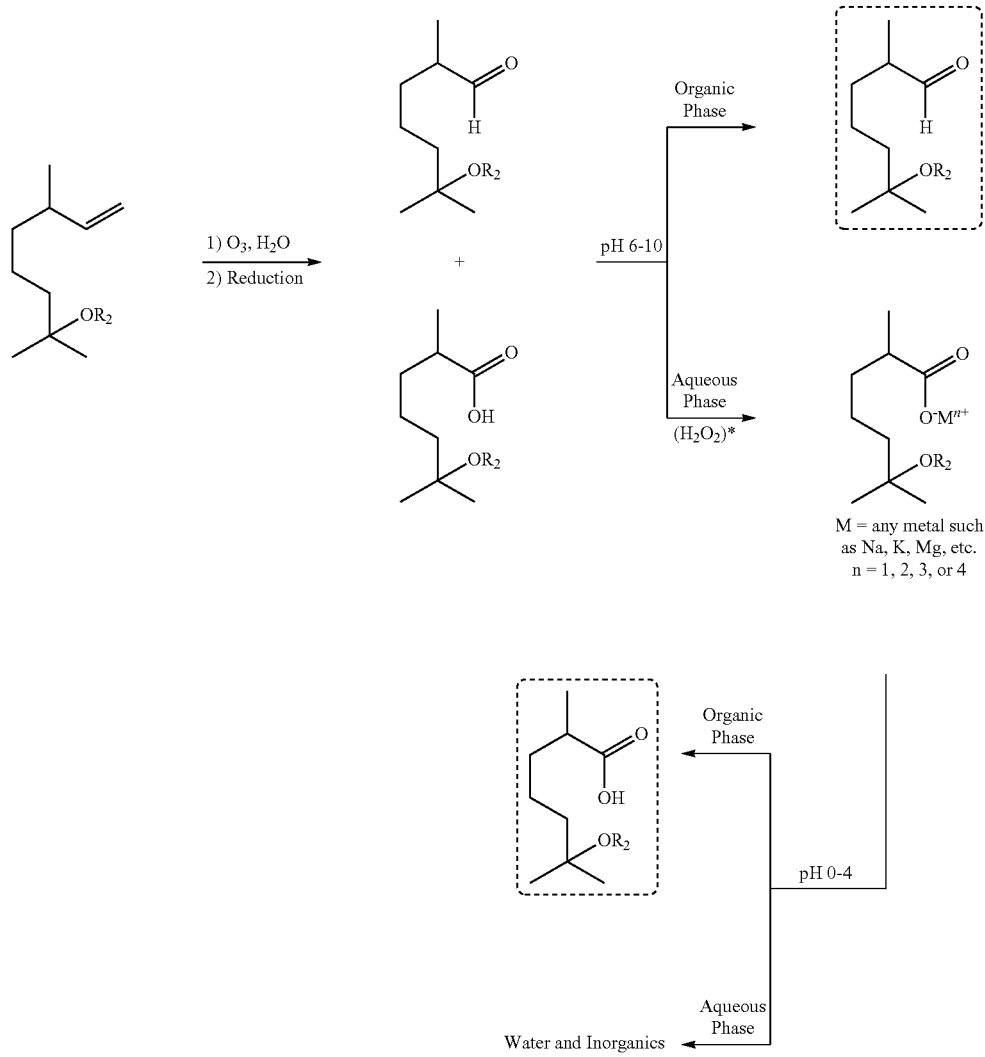

Scheme 2

M = any metal such as Na, K, Mg, etc.
n = 1, 2, 3, or 4

*$H_2O_2$ or other oxidant is optionally dded to the basic aqueous mixture and stirred to convert any trace aldehyde present into acid/acid salt.

In some embodiments, reductive ozonolysis may be performed in an aqueous mixture without a buffer, and the pH value of the resultant reaction mixture may be low, and may be from about 1 to about 3. An alkaline compound, for example $NaHCO_3$, $Na_2CO_3$, NaOH, $K_2CO_3$, KOH, and/or dibasic phosphate, or other inexpensive bases, may be added to adjust the pH value to between about 6 and about 10. Following pH adjustment, the reaction mixture may then be phase separated in the presence of water to give an organic As illustrated in Scheme 1 above, the acids obtained can then be esterified to generate esters. Additionally, these esters can undergo a subsequent or tandem elimination reaction in the presence of an acid to generate ester-olefins, such as the compounds of formulae (II) and (III). In accordance with some embodiments, the acids/esters of formula (II) or (III) obtained can further be converted to the compounds of formula (IV):

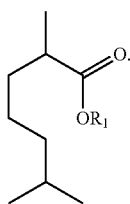

(IV)

For example, the acids/esters of formula (II) or (III) can be reduced, such as via a hydrogenation reaction, to generate an acid/ester-paraffin, such as the compounds of formula (IV).

In some embodiments, methoxycitronellene (i.e., 7-methoxy-3,7-dimethyloct-1-ene) may be combined with water and cooled to, for example, about 10° C. while stirring rapidly in, for example, a jacketed glass reactor equipped with an overhead stirrer and controlled gas diffusion. Ozone, for example 5-7% by weight in oxygen, may then be diffused into the mixture until all of the starting material is consumed. The reaction temperature may be maintained, and may be maintained at a temperature below about 22° C. The reaction vessel may then be purged with $N_2$ and the mixture may be transferred into a high-pressure reactor and charged with palladium black, for example, 0.2% by weight. The reaction mixture may then be stirred under a hydrogen atmosphere (for example, about 300 psi) at a suitable temperature (for example, about 75° C.) until the peroxide value of the reaction mixture approaches zero, which may be, for example, about 2.5 hours. The mixture may then be filtered to remove the catalyst and placed in a reparatory funnel. The organic phase may be separated and washed with deionized water to afford a solution containing methoxymelonal and its corresponding acid, i.e., 6-methoxy-2,6-dimethylheptanoic acid. Next, the organic phase may be further extracted with a basic aqueous solution, for example, 10% (aq.) $Na_2CO_3$, to separate any residual acid byproduct from the aldehyde. The aqueous phase may then be charged with a peroxide, for example, hydrogen peroxide. An acid, for example, $NaHSO_3$, may then be added to the reaction mixture until no excess peroxide can be measured with KI starch strips. The aqueous mixture may then be acidified to a pH of about 2 to about 3 by, for example, adding 6N (aq.) HCl. Following the pH adjustment, an organic phase is obtained, which contains 6-methoxy-2,6-dimethylheptanoic acid. The acidic aqueous phase can be further extracted using, for example, EtOAc, to obtain an additional amount of the desired acid product after evaporation.

In one embodiment, 6-methoxy-2,6-dimethylheptanoic acid may be dissolved in methanol, and an acid, for example conc. $H_2SO_4$, is added to the stirring reaction mixture. The mixture may be stirred at room temperature overnight, then heated, for example, to about 50° C. for about 2 hours, and refluxed for about an additional 3 hours. The solvent may be removed via evaporation and the resulting crude residue may then be dissolved in EtOAc. The organic solution can then be washed with, for example, 10% (aq.) $Na_2CO_3$ and then evaporated to afford methyl 6-methoxy-2,6-dimethylheptanoate.

In one embodiment, 6-methoxy-2,6-dimethylheptanoic acid may be dissolved in EtOH and charged with an acid, which may be, for example, Tosic Acid. The reaction mixture may be stirred at room temperature until all the starting material is consumed, which may be a time period of about 1 to about 5 days, for example, about 3 days. The reaction mixture may then be concentrated in the presence of silica gel to obtain a mixture of ethyl 2,6-dimethylhept-5-enoate and ethyl 2,6-dimethylhept-6-enoate.

In accordance with embodiments, the acid or ester product from the disclosed methods of the invention may be greater than about 80% pure and may be, for example, greater than about 90% pure, greater than about 95% pure, greater than about 98% pure, or greater than about 99% pure. $^1H$ NMR and gas chromatography can be used to characterize the desired acid or ester product. For example, $^1H$ NMR and gas chromatography may be used to confirm that the acid or ester product is free of aldehydic material or starting material. $^1H$ NMR and gas chromatography may also be used to confirm the level of impurities present in the acid or ester product. Impurities may include, but are not limited to, starting material terpenes such as methoxycitronellene, hydroxycitronellene, acetoxycitronellene and alkoxycitronellenes and their aldehydic products, such as methoxymelonal, as well as other reaction byproducts. $^1H$ NMR and gas chromatography may be used to confirm that these impurities are present in an amount less than about 20%, less than about 10%, less than about 5%, less than about 2%, or less than about 1%.

The invention also relates to a process of separating an acid and an aldehyde following a reductive ozonolysis of an olefin, for example a terpene. A representative process scheme is shown in Scheme 2 above.

In one embodiment, the ozone used in the ozonolysis is generated by electrolyzing water.

In some embodiments, the product of the method of the invention may have an overall yield of no less than about 60%, no less than about 70%, no less than about 80%, or no less than about 90%.

In some embodiments, the product of the method of the invention may contain more than about 80% of compound of formula (I). In some embodiments, the product of the method of the invention may contain more than about 85%, more than about 90%, more than about 92%, more than about 95%, more than about 97%, more than about 98%, more than about 98.5%, or more than about 99% of compound of formula (I). In accordance with embodiments, the product may contain less than about 20%, less than about 15%, less than about 10%, less than about 8%, less than about 3%, less than about 2%, less than about 1.5%, or less an about 1% impurities.

In some embodiments, the product of the method of the invention may contain more than about 80% of compound of formulae (II) and/or (III). In some embodiments, the product of the method of the invention may contain more than about 85%, more than about 90%, more than about 92%, more than about 95%, more than about 97%, more than about 98%, more than about 98.5%, or more than about 99% of compound of formulae (II) and/or (III).

In accordance with these embodiments, the product may contain less than about 20%, less than about 15%, less than about 10%, less than about 8%, less than about 3%, less than about 2%, less than about 1.5%, or less an about 1% impurities.

It will be appreciated that the methods disclosed herein are suitable for both large-scale and small-scale preparations of the desired compounds. In preferred embodiments of the methods described herein, the compounds of formula (I) or the compounds of formula (II) may be prepared on a large scale, for example on an industrial production scale rather than on an experimental/laboratory scale. For example, the methods of the disclosure may advantageously allow for the preparation of batches of at least about 1 g product, at about least 5 g product, at least about 10 g product, at least about 100 g product, at least about 1 kg product, at least about 10 kg product, or at least about 100 kg of product.

The invention also relates to a compound of formulae (I), (II), (III) or (IV) below and salts thereof:

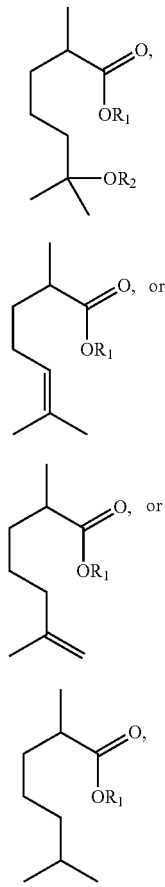

wherein $R_1$ is one of H, an unsubstituted or substituted $C_1$-$C_{10}$ alkyl, or an unsubstituted or substituted $C_2$-$C_{10}$ alkenyl, and $R_2$ is one of H, or an unsubstituted or substituted $C_1$-$C_{10}$ alkyl, or $COR_a$, in which $R_a$ is H or an unsubstituted or substituted $C_1$-$C_{10}$ alkyl.

For example, in accordance with embodiments, $R_1$ may be a substituted or unsubstituted alkyl having 1, 2, 3, 4, 5, 6, 7, 8, 9, or 10 carbon atoms, or an unsubstituted alkenyl having 2, 3, 4, 5, 6, 7, 8, 9, or 10 carbon atoms and one, two, or three carbon-carbon double bonds.

In some embodiments, $R_2$ may be H or a substituted or unsubstituted alkyl having 1, 2, 3, 4, 5, 6, 7, 8, 9, or 10 carbon atoms.

In some embodiments, $R_2$ may be $COR_a$, in which $R_a$ is H or an unsubstituted or substituted alkyl having 1, 2, 3, 4, 5, 6, 7, 8, 9, or 10 carbon atoms.

In some embodiments, formulae (I), (II), (III), or (IV), $R_1$ may be an unsubstituted $C_1$-$C_3$ alkyl, for example an alkyl having 1, 2, or 3 carbon atoms, or unsubstituted $C_2$-$C_3$ alkenyl, for example an alkenyl having 2 or 3 carbon atoms such as an allyl.

In some embodiments, formula (I), (II), (III), or (IV) $R_1$ may be an unsubstituted $C_3$-$C_9$ alkyl, for example an alkyl having 3, 4, 5, 6, 7, 8, or 9 carbon atoms.

In some embodiments of formula (I), $R_2$ may be an unsubstituted $C_1$-$C_3$ alkyl for example an alkyl having 1, 2, or 3 carbon atoms, or $COCH_3$.

In some embodiments of formula (I), $R_2$ may be an unsubstituted $C_3$-$C_9$ alkyl (e.g., alkyl having 3, 4, 5, 6, 7, 8, or 9 carbon atoms).

In some embodiments, the compounds of formulae (I), (II), (III), or (IV), may include

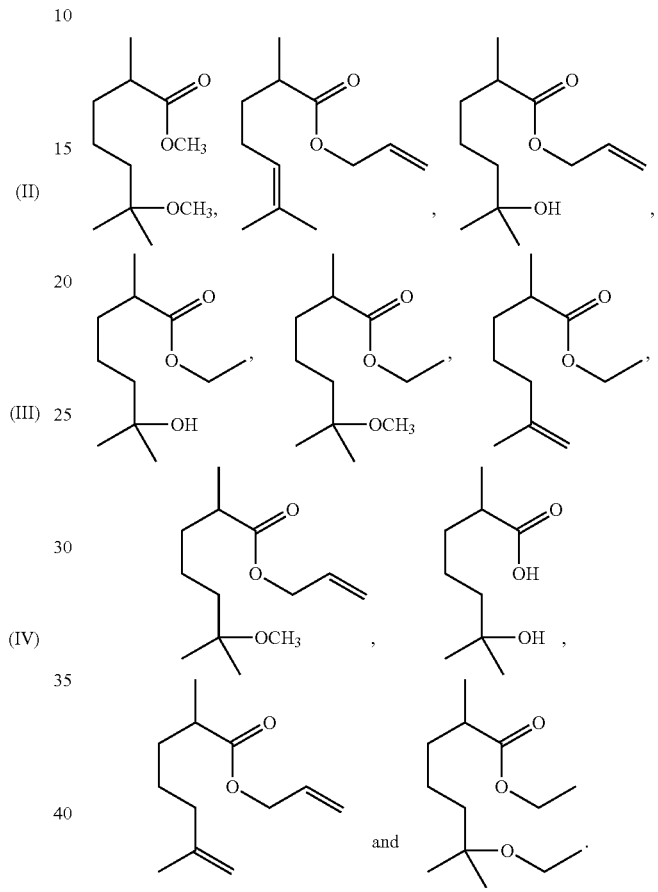

Unless otherwise indicated, it is to be understood that the terminology used herein is for the purpose of describing particular embodiments only and is not intended to be limiting. In this specification and in the claims that follow, reference will be made to a number of terms, which shall be defined to have the definitions set forth below.

As used herein, the phrase "having the formula" or "having the structure" is not intended to be limiting and is used in the same way that the term "comprising" is commonly used.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116). In some formulae of the present application, one or more chiral centers are identified by an asterisk placed next to the chiral carbon. In other formulae, no chiral center is identified, but the chiral isomers are nonetheless covered by these formulae.

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Some compounds of the present invention can exist in a tautomeric form which is also intended to be encompassed within the scope of the present invention. "Tautomers" refers to compounds whose structures differ markedly in arrangement of atoms, but which exist in easy and rapid equilibrium. It is to be understood that the compounds of the invention may be depicted as different tautomers. It should also be understood that when compounds have tautomeric forms, all tautomeric forms are intended to be within the scope of the invention, and the naming of the compounds does not exclude any tautomeric form. Further, even though one tautomer may be described, the present invention includes all tautomers of the present compounds.

As used herein, the term "salt" can include acid addition salts including hydrochlorides, hydrobromides, phosphates, sulfates, hydrogen sulfates, alkylsulfonates, arylsulfonates, acetates, benzoates, citrates, maleates, fumarates, succinates, lactates, and tartrates; alkali metal cations such as $Na^+$, $K^+$, $Li^+$, alkali earth metal salts such as $Mg^{2+}$ or $Ca^{2+}$, or organic amine salts, or organic phosphonium salts.

The term "alkyl" as used herein refers to a branched or unbranched saturated hydrocarbon group typically although not necessarily containing 1 to about 10 carbon atoms, such as methyl, ethyl, n-propyl, isopropyl, n-butyl, isobutyl, t-butyl, octyl, and the like.

The term "alkenyl" as used herein refers to a branched or unbranched saturated or unsaturated hydrocarbon group typically although not necessarily containing 2 to about 10 carbon atoms and 1-8 carbon-carbon double bonds, such as ethylene, n-propylene, isopropylene, n-butylene, isobutylene, t-butylene, octylene, and the like.

By "substituted" as in "substituted alkyl," "substituted alkenyl," and the like, it is meant that in the alkyl, alkenyl, or other moiety, at least one hydrogen atom bound to a carbon atom is replaced with one or more non-hydrogen substituents, e.g., by a functional group.

Examples of functional groups include, without limitation: halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O$^-$)), phospho (—$PO_2$), phosphino (—$PH_2$), mono- and di-($C_1$-$C_{24}$ alkyl)-substituted phosphino, mono- and di-($C_5$-$C_{20}$ aryl)-substituted phosphino; and the hydrocarbyl moieties such as $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties, including but not limited to those specifically enumerated above.

In the present specification, the structural formula of the compound may represent a certain isomer, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention.

Fragrance Formulation

The compounds of the present invention may have unique aromas. Compounds of formula (I) have been found to have a medium strength odor with rose and geranium notes mingled with fruity notes of banana and mango, whereas compounds of formula (II) and (III) exhibit a strong, sweet, floral odor with a hint of lavender and a touch of fruit, reminiscent of banana. As a result, the disclosed compounds may be advantageously used in fragrance applications.

Compounds of formula (I), (II) (III), and (IV) may be used alone, or more preferably, in combination with one or more known fragrance ingredients to achieve a desired aroma. The compounds of the present invention may be used to create, enhance, or modify a fragrance composition. In addition to being used in fragrance applications, the compounds of present invention may be used in food flavorings, and may, for example, be used to impart green, sweet, tropical fruit-like aromas and tastes to edible products. The compounds of the present invention can be used in a broad range of fragrance applications. For example, compounds having the formulae of the present invention may be used in perfumes, household products, laundry products, personal care products and cosmetics. The disclosed compounds may be employed in varying amounts, depending upon the specific fragrance application, the nature and amount of other odor carrying ingredients present, and the desired aroma of the product.

As used herein, "perfume composition" means a mixture of fragrance materials, including auxiliary substances if desired, dissolved in a suitable solvent or mixed with a powdery substrate used to impart a desired odor to a product. Examples of products having perfume compositions include, but are not limited to, perfumes, soaps, detergents, air fresheners, room sprays, pomanders, candles, cosmetics, such as creams, ointments, toilet waters, pre- and aftershave lotions, talcum powders, hair-care agents, body deodorants and anti-perspirants. Fragrance materials and mixtures of fragrance materials that may be used in combination with the disclosed compounds for the manufacture of a perfume compositions include, but are not limited to, natural products including essential oils, absolutes, resinoids, resins, and concretes, and synthetic fragrance materials which include, but are not limited to, hydrocarbons, alcohols, aldehydes, ketones, ethers, acids, esters, acetals, ketals, and nitriles, including both saturated and unsaturated compounds and aliphatic carbocyclic and heterocyclic compounds.

Examples of the fragrance materials which may be used in combination with the disclosed include but are not limited to, geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenylcarbinyl acetate, p-tert-butylcyclohexyl acetate, isononyl acetate, vetiveryl acetate, vetiverol, alpha-hexylcinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentyl-cyclopentane, 2-n-heptylcyclopentanone, 3-methyl-2-pentyl-2-cyclopentenone, n-decanal, n-dodecanal, 9-decen-1-01, phenoxyethylisobutyrate, phenylacetaldehydedimethylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, aromatic nitromusks.

Auxiliary substances and solvents which may be used in perfume compositions containing compounds according to the present invention include, but are not limited to, ethanol, isopropanol, dipropylene glycol, dipropyleneglycol monomethyl ether, and diethylphthalate.

The quantities of the disclosed compounds used in a perfume composition or a product to be perfumed may vary according to the nature of the product, the nature and quantity of the other fragrance materials in the perfume composition, and on the desired odor effect. For example, a non-limiting concentration of the disclosed compounds in a given fragrance composition may be from about 0.005% to about 25%, from about 0.05% to about 10%, or more particularly, from about 0.1% to about 5%. The use of compounds having formulae of the present invention in fragrance compositions is illustrated in Examples 3 and 4.

The function and advantages of these and other embodiments will be more fully understood from the following non-limiting examples. The examples are intended to be illustrative in nature and are not to be considered as limiting the scope of the embodiments discussed herein.

EXAMPLES

Example 1: Synthesis of 6-Methoxy-2,6-Dimethylheptanoic Acid and Esters

Acid Isolation

Methoxycitronellene (i.e., 7-methoxy-3,7-dimethyloct-1-ene, 350 g, 0.486 mol) was combined with water (700 g) and cooled to 10° C. while stirring rapidly in a jacketed glass reactor equipped with an overhead stirrer and controlled gas diffusion. 5-7% by weight ozone in oxygen was diffused into the mixture at a flow rate of 10 L/min over 110 minutes until all of the starting material was consumed, while maintaining a reaction temperature below 22° C. The reaction vessel was then purged with $N_2$ and the mixture was transferred into a high-pressure reactor and charged with palladium black (0.2% by weight). The reaction mixture was stirred under hydrogen atmosphere (300 psi) at 75° C. for 2.5 hours until the peroxide value of the reaction mixture approached zero. The mixture was then filtered to remove the catalyst and placed in a reparatory funnel. The organic phase was separated and washed with deionized water (150 mL) to afford a solution containing a crude material consisting predominantly of methoxymelonal and its corresponding acid, i.e., 6-methoxy-2,6-dimethylheptanoic acid (336 g).

The organic phase was further extracted with 10% (aq.) $Na_2CO_3$ to remove any residual acid byproduct. The phases were separated and the organic phase contained clean methoxymelonal (275 g). The aqueous phase was charged with hydrogen peroxide (2.4 g, 30 wt. %) and stirred at room temperature overnight. The next day, $NaHSO_3$ was added to the reaction mixture until no excess peroxide could be measured with KI starch strips. The aqueous mixture was acidified to a pH of about 2-3 with the slow addition of 6N (aq.) HCl. Following the pH adjustment, an organic phase separated out, which contained almost exclusively the corresponding terpene-derived acid, 6-methoxy-2,6-dimethylheptanoic acid (45.1 g). $^1$H NMR for this material is shown in FIG. 1. The acidic aqueous phase was extracted again using EtOAc to obtain an additional amount (4.5 g) of the desired acid product after evaporation.

Figure 2:
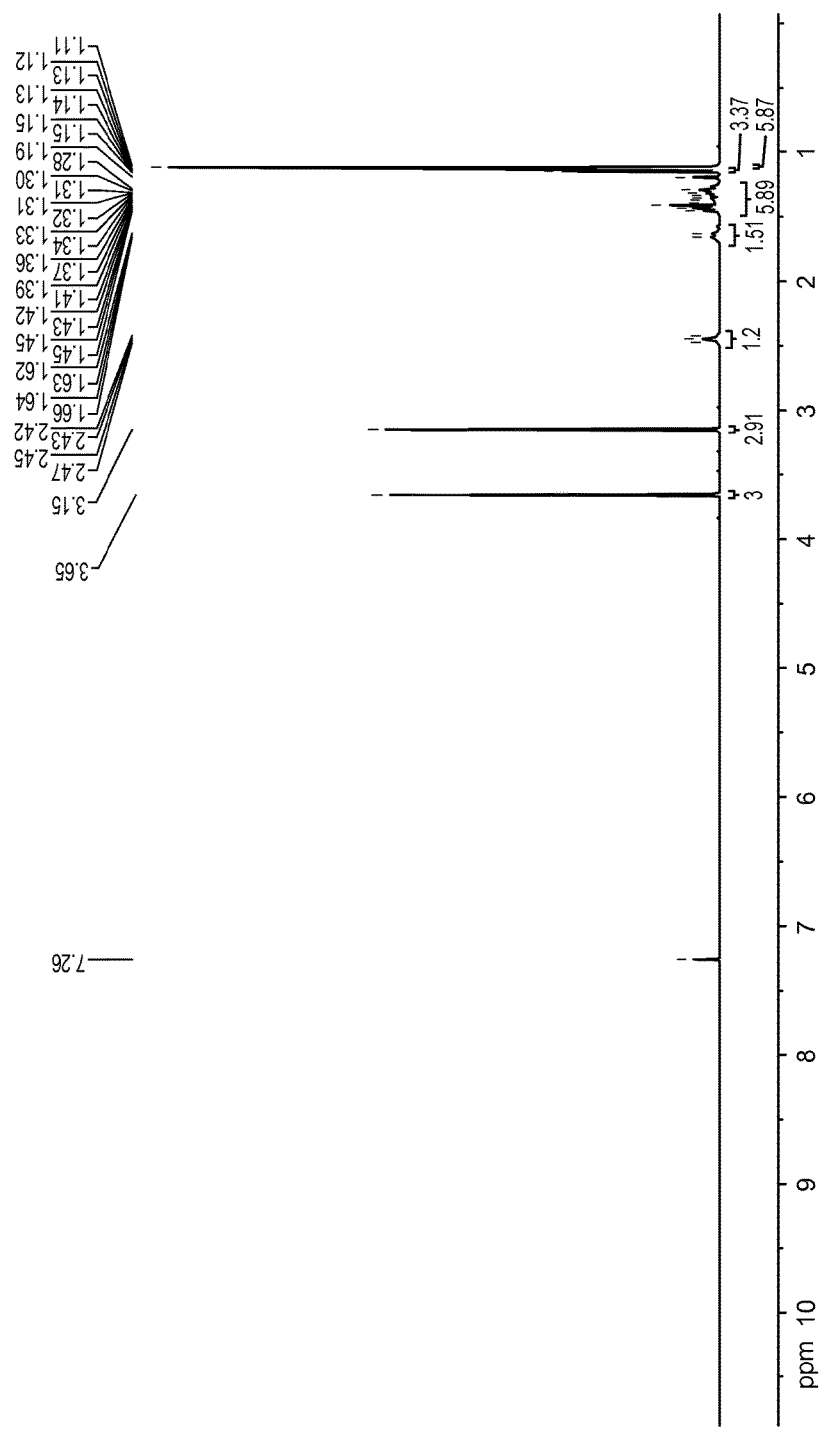
FIG. 2 is a $^1$H NMR spectrum of methyl 6-methoxy-2,6-dimethylheptanoate.

Esterification 6-methoxy-2,6-dimethylheptanoic acid (1.7 g, 0.9 mmol) was dissolved in MeOH (10 mL) and 2 drops of conc. $H_2SO_4$ were added to the stirring reaction mixture. The mixture was stirred at room temperature overnight, then heated to 50° C. for 2 hours, and refluxed for an additional 3 hours. The solvent was removed via evaporation and the resulting crude residue was dissolved in EtOAc (50 mL). The organic solution was washed with 10% (aq.) $Na_2CO_3$ (50 ml of 10% by weight in water) and then evaporated to afford the methyl ester, i.e., methyl 6-methoxy-2,6-dimethylheptanoate (1.6 g). $^1$H NMR of this material is shown in FIG. 2.

Figure 3:
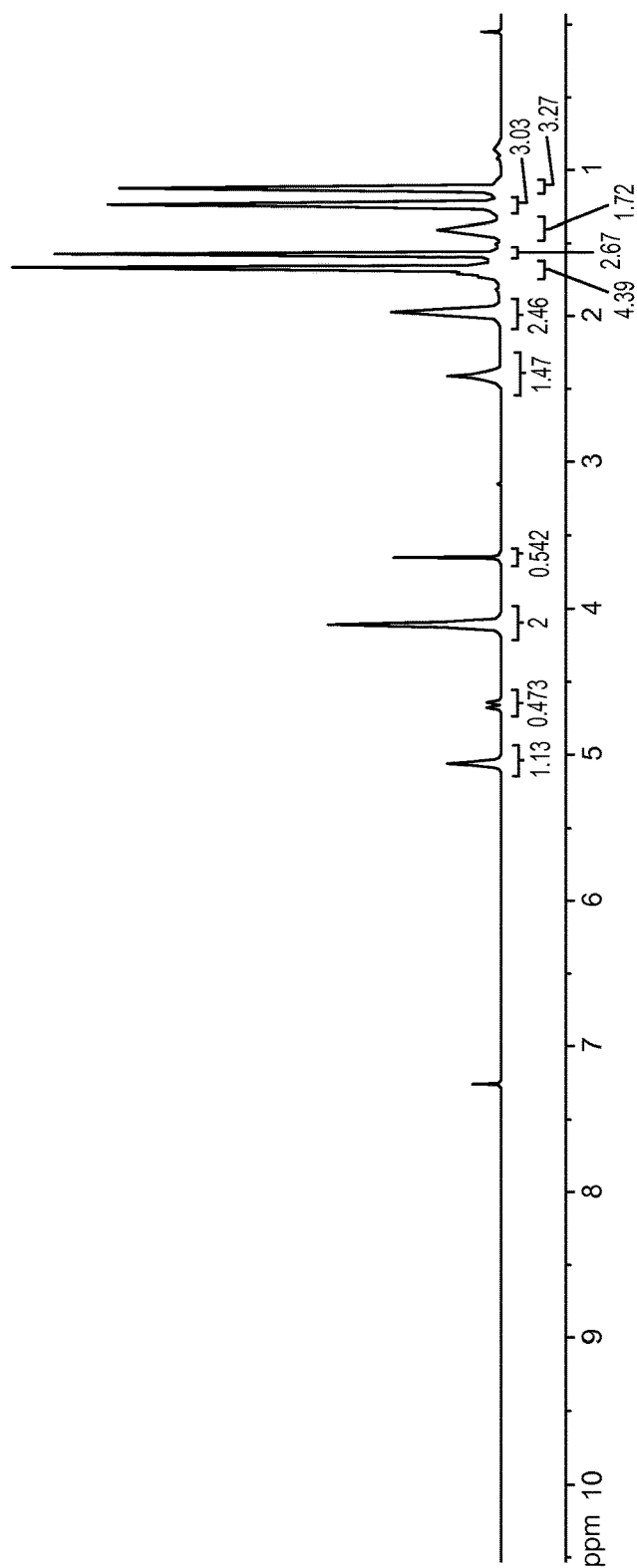
FIG. 3 is a $^1$H NMR spectrum of a mixture of ethyl 2,6-dimethylhept-5-enoate and ethyl 2,6-dimethylhept-6-enoate.

Esterification and Elimination 6-methoxy-2,6-dimethylheptanoic acid (4.0 g) was dissolved in EtOH (20 mL) and charged with tosic acid (400 mg). The reaction mixture was stirred at room temperature for 3 days until all of the starting material was consumed. The reaction mixture was concentrated in the presence of silica gel, which was used in silica gel chromatography (2-5% gradient of EtOAc in heptane) to obtain a mixture of ethyl 2,6-dimethylhept-5-enoate and ethyl 2,6-dimethylhept-6-enoate (1.5 g). $^1$H NMR of the product is shown in FIG. 3 (note there was some methyl ester in the mixture as well due to methanol contained in EtOH used as an EtOH denaturant).

Example 2: Additional Analogs

6-Hydroxy-2,6-dimethylheptanoic acid was prepared in a fashion similar to that described in Example 1, using hydroxycitronellene (i.e., 2,6-dimethyloct-7-en-2-ol) as a starting material. Several ester derivatives of 6-hydroxy-2,6-dimethylheptanoic acid were also prepared in a fashion similar to that described in Example 1.

Example 3: Topical Fruit Fragrance Formulation

A tropical fruit fragrance having hints of floral notes and freshness of lavender was prepared comprising compounds having the formulae of the present invention. A compound having formula (I), methyl 6-methoxy-2,6-dimethylheptanoate, and a compound having formula (II), methyl 2,6-dimethylhept-5-ene-carboxylate, were prepared according to the methods disclosed. A 10% solution in dipropylene glycol (DPG) of each of the compounds was then added to a perfume composition. Table 1 lists the composition's ingredients and their corresponding part of the total composition.

TABLE 1

| Ingredient | Parts (g) |
| --- | --- |
| Allyl Caproate | 105 |
| Allyl Heptoate | 75 |
| Amyl Cinn Ald | 7.5 |
| Benzyl Acetate | 7.5 |
| Coumarin | 7.5 |
| Davana Oil | 15 |
| Ethyl Aceto Acetate | 30 |
| Ethyl Caproate | 9 |
| Ethyl Caprylate | 27 |
| Linalol | 38 |
| Maltol | 3 |
| Mandarin Oil | 30 |
| Octalactone Gamma | 2 |
| Orange Oil | 226 |
| Orange Terpenes | 45 |
| Undecalactone Gamma | 15 |
| Tangerine Oil | 76 |
| Terpineol | 3 |
| Vanillin | 7.5 |
| DPG | 201 |
| Methyl 6-methoxy-2,6-dimethyl-heptanoate 10% DGP | 30 |
| Methyl 2,6-dimethylhept-5-ene-oate 10% DGP | 40 |
| Total | 1000.0 |

The fragrance composition corresponding to Table 1 demonstrated that the addition of a compound having formula (I), specifically methyl 6-methoxy-2,6-dimethylheptanoate, and a compound having formula (II), specifically methyl 2,6-dimethylhept-5-ene-oate, provided a fresh and exotic tropical fruit composition with clean floral undertones.

Example 4: Green, Fruity, Floral Fragrance Formulation

A green, fruity, floral fragrance was prepared comprising compounds having the formulae of the present invention. A compound having formula (II), methyl 2,6-dimethylhept-5-ene-oate, was prepared according to the methods disclosed and then added to a perfume composition. Table 2 lists the composition's ingredients and their corresponding part of the total composition.

TABLE 2

| Ingredient | Parts (g) |
| --- | --- |
| Amyl Salicylate | 13 |
| Clove Oil | 0.5 |
| Coumarin | 10 |
| Dihydro Myrcenol | 20 |
| DPG | 26.3 |
| Galaxolide 50 BB | 128 |
| Geranyl Acetate | 0.5 |
| Hedione | 34 |
| Hydroxycitronellal 10% DGP | 1 |
| Indole 10% | 1 |
| Ionone Beta | 0.5 |
| Iso E Super | 260 |
| Lemon Oil | 100 |
| Linalol | 19 |
| Linalyl Acetate | 55 |
| Lyral | 45 |
| Mandarin Oil | 15 |
| Methyl Anthranilate 10% DGP | 1 |
| Methyl Ionone Gamma | 3 |
| Nutmeg Oil | 12 |
| Patchouli Oil | 16 |
| Sandalore | 30 |
| Thyme Oil White | 0.3 |
| Timberol | 3 |
| Tonalide | 108 |
| Vertofix Coeur | 90 |
| Triplal | 0.4 |
| Methyl 2,6-dimethylhept-5-ene-oate 10% DGP | 7.5 |
| Total | 1000.0 |

The fragrance composition corresponding to Table 2 demonstrated that the addition of a compound having formula (II), specifically methyl 2,6-dimethylhept-5-ene-oate, provided a fresh and clean aroma with green floral notes.

Having now described some illustrative embodiments of the invention, it should be apparent to those skilled in the art that the foregoing is merely illustrative and not limiting, having been presented by way of example only. The invention can therefore be embodied in other specific forms without departing from the spirit or essential characteristics thereof.

Those skilled in the art should appreciate that the parameters and specific compounds described herein are exemplary and that the actual reaction parameters and/or compounds synthesized and used will depend on the application in which the methods and compounds of the invention are used. Those skilled in the art should also recognize or be able to ascertain, using no more than routine experimentation, equivalents to the specific embodiments of the invention. It is therefore to be understood that the embodiments described herein are presented by way of example only and that the scope of the invention is thus indicated by the appended claims and equivalents thereto, and that the invention may be practiced otherwise than as specifically described in the foregoing description.

As used herein, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

The entire disclosure of each of the patent documents and scientific articles referred to herein is incorporated by reference in its entirety for all purposes.

What is claimed is:

1. A compound selected from the group consisting of:

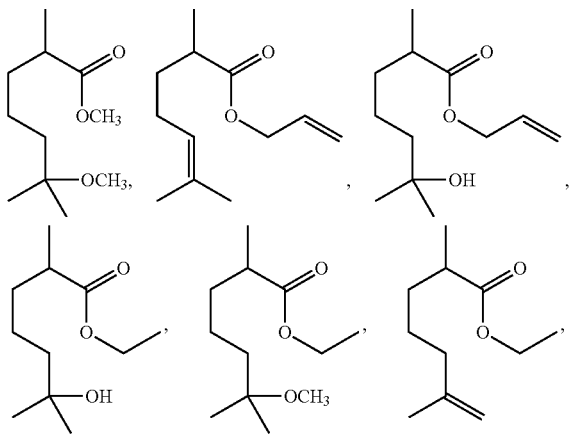

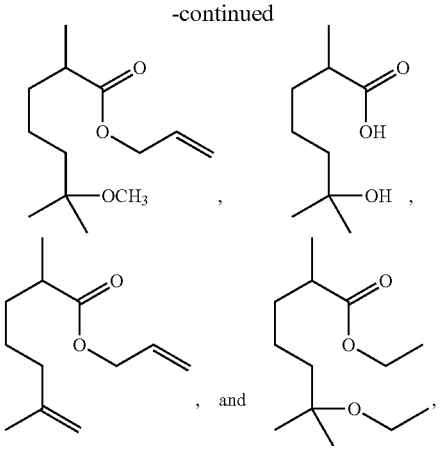

and salts thereof.

2. A perfume composition comprising one or more compounds of claim 1.

3. The perfume composition of claim 2 comprising at least one of:

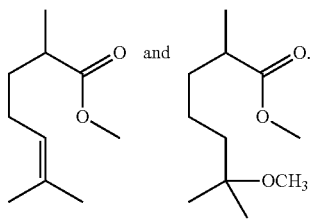

4. A food product comprising a flavoring comprising one or more compounds of claim 1.

5. The food product of claim 4, wherein the flavoring comprises at least one of

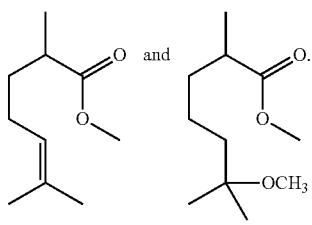

* * * * *